United States Patent

Hamashima et al.

[11] 4,130,557
[45] Dec. 19, 1978

[54] METHOD FOR THE HYDROLYSIS OF AZETIDINOTHIAZOLINE COMPOUNDS

[75] Inventors: Yoshio Hamashima, Kyoto; Teruji Tsuji, Takatsuki; Mitsuru Yoshioka, Toyonaka; Masayuki Narisada, Ibaraki; Taichiro Komeno; Hiroshi Tanida, both of Osaka; Wataru Nagata, Nishinomiya, all of Japan

[73] Assignee: Shionogi & Co., Ltd., Japan

[21] Appl. No.: 653,629

[22] Filed: Jan. 29, 1976

[30] Foreign Application Priority Data

Jan. 30, 1975 [JP] Japan .................. 50-13157

[51] Int. Cl.² .............. C07D 205/08; C07D 403/04; B01J 1/10
[52] U.S. Cl. ................... 260/239 A; 260/326 E; 260/326 S; 204/158 R
[58] Field of Search ..................... 260/239 A

[56] References Cited

U.S. PATENT DOCUMENTS 2,581,493 1/1952 Lyon et al. ................. 260/609 C

FOREIGN PATENT DOCUMENTS 2230456 1/1974 Fed. Rep. of Germany ...... 260/239 A

OTHER PUBLICATIONS

Sachs, Chem. Abs. 16, 905 (1922).
Sachs et al, Chem. Abs. 20, 1605 (1926).
Klason, Chem. Ber. 20, 3407-3413 (1887).
Reid et al., "Organic Chem. of Bivalent Sulfur" vol. 1, p. 142.
Lattrell et al. II, Ann. Chem. 1937-1954 (1974).
Lattrell, Ann. Chem. 1974, 1937-1954.

*Primary Examiner*—Jose Tovar
*Assistant Examiner*—Mark L. Berch
*Attorney, Agent, or Firm*—Wenderoth, Lind & Ponack

[57] ABSTRACT

A process for preparing compounds having the formula:

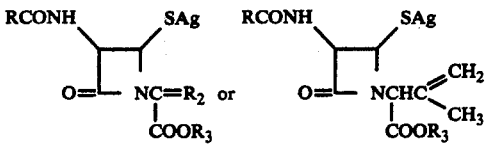

wherein R is phenoxymethyl or benzyl;
$R_2$ is 1-methoxyethylidene, 1-hydroxyethylidene, or 1,1-dimethoxyethylidene; and
$R_3$ is trichloroethyl, diphenylmethyl, p-nitrobenzyl, trityl, phenyl, naphthyl, or trimethylstannyl;
which comprises treating a compound of the following formula:

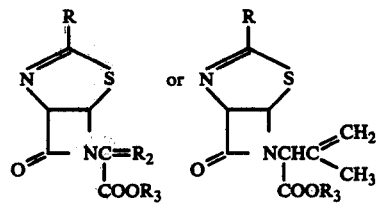

where R, $R_2$ and $R_3$ are as defined above,
with $AgClO_4$, $AgBF_4$, $AgIO_4$, $AgPF_6$, $CF_3COOAg$, $CH_3SO_3Ag$, $CF_3SO_3Ag$, $CH_3COOAg$, or $AgNO_3$ in aqueous dioxane, aqueous tetrahydrofuran or mixtures thereof.

5 Claims, No Drawings

METHOD FOR THE HYDROLYSIS OF AZETIDINOTHIAZOLINE COMPOUNDS

This invention relates to a process for the hydrolysis of an acylthio group represented by the following reaction scheme:

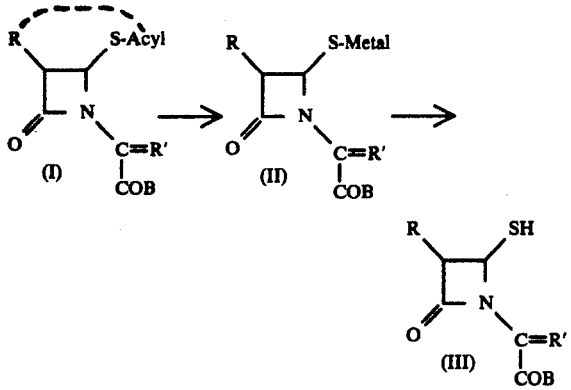

wherein R is an amino or substituted amino; Acyl is an acyl group, B is a hydroxy group or carboxy protecting group; Metal is a metal belonging to the group Ib of IIb of the periodical table; R' is ethyl, ethylene, or ethylidene group optionally substituted by alkyl or alkoxy containing 1 to 3 carbon atoms, hydroxy, alkoxyalkyl containing 2 to 5 carbon atoms, halogen, carboxylic, sulfonic, or carbonic acyloxy containing 1 to 8 carbon atoms, or amino bearing hydrogen, alkyl containing 1 to 8 carbon atoms, or alkoxyalkyl. The broken line between R and Acyl shows the acyl carbonyl can be combined with amino R to give an azetidinothiazdine ring system.

In the above reaction scheme, the Acyl of the acylthio at position 4 can be that derived from organic acids containing 1 to 12 carbon atoms, for example, carboxylic acid (e.g. alkanoic acid, alkenoic acid, alkynoic acid, cycloalkanoic acid, aralkanoic acid, aralkenoic acid, aromatic carboxylic acid, or other carboxylic acids optionally substituted by e.g. an inert group selected from halogen, alkyl, phenyl, halophenyl, alkoxy, aryloxy, acyloxy and oxo), sulfonic acid, sulfinic acid, phosphonic acid, or other organic acids; or from inorganic acid e.g. carbonic acid, sulfuric acid, phosphoric acid, halogenic acid, hydrohalogenic acid, or other inorganic acids.

The amino substituents in the group R at position 3 can be an amino substituent constituting known side chains in the chemistry of natural or synthetic penicillins or cephalosporins, or their equivalents. The group can widely be varied, because it generally has a less direct relationship with the hydrolysis of 4-acylthio group. It can be an acyl, hydrocarbyl, hydrocarbylidene, silyl, sulfenyl, or like conventional amino substituents in the field of cephalosporin or penicillin chemistry, and containing up to 20 carbon atoms.

Representative acyl includes following groups:
(1) alkanoyl containing from 1 to 5 carbon atoms;
(2) haloalkanoyl containing from 2 to 5 carbon atoms;
(3) azidoacetyl;
(4) cyanoacetyl;
(5) acyl groups of the formula:

Ar—CQQ'—CO— in which Q and Q' are each hydrogen or methyl; and Ar is phenyl, dihydrophenyl, or a monocyclic heterocyclic aromatic group containing from 1 to 4 hetero atoms selected from nitrogen, oxygen, and/or sulfur atoms, and may optionally be substituted by an inert group e.g. an alkyl or alkoxy group containing from 1 to 3 carbon atoms, chlorine, bromine, iodine, fluorine, trifluoromethyl, hydroxy, cyano, aminomethyl, amino, or nitro;
(6) acyl groups of the formula:

Ar—G—CQQ'—CO— in which G is an oxygen or sulfur; and Ar, Q, and Q' are as defined above;
(7) acyl groups of the formula:

Ar—CHT—CO— in which Ar is as defined above; and T is i) amino, ammonium, amino substituted by such conventional amino substituents as benzyloxycarbonyl, alkoxycarbonyl containing from 1 to 4 carbon atoms, cyclopentyloxycarbonyl, cyclohexyloxycarbonyl, benzhydryloxycarbonyl, cyclopropylmethoxycarbonyl, methanesulfonylethoxycarbonyl, triphenylmethyl, 2,2,2-trichloroethoxycarbonyl, guanidylcarbamoyl, optionally substituted ureido carbonyl, alkanoyl containing from 1 to 5 carbon atoms, pyronecarbonyl, thiopyronecarbonyl, pyridonecarbonyl, homo- or heterocyclic monocyclic aromatic acyl optionally substituted by hydroxy, lower alkanoyloxy containing from 1 to 3 carbon atoms, halogen, trifluoromethyl or alkyl containing from 1 to 3 carbon atoms, aminoalkyl containing from 1 to 3 carbon atoms, halogen, trifluoromethyl, or alkyl containing from 1 to 3 carbon atoms, or hydroxyalkyl containing from 1 to 3 carbon atoms, or amino protected in the forms of phthalimido, or of enamino derived from acetoacetates, acetylacetone, acetacetamido, or acetoacetonitrile, ii) hydroxy or acyloxy containing from 1 to 7 carbon atoms, iii) carboxy or alkoxycarbonyl containing from 2 to 7 carbon atoms, indanyloxycarbonyl, phenoxycarbonyl, or iv) azido, cyano, carbamoyl, alkoxysulfonyl, sulfo, or alkoxysulfonyl;
(8) 2-sydnon-3-alkanoyl containing from 3 to 5 carbon atoms;
(9) (2- or 4-pyridon-1-yl)acetyl;
(10) 5-aminoadipoyl, 5-aminoadipoyl protected at the amino group by aroyl or alkanoyl containing from 1 to 10 carbon atoms, chloroalkanoyl containing from 1 to 5 carbon atoms, or by alkoxycarbonyl containing from 2 to 10 carbon atoms; or 5-aminoadipoyl protected at the carboxy group by benzhydryl, 2,2,2-trichloroethyl, trialkylsilyl, alkyl containing from 1 to 6 carbon atoms, nitrobenzyl, or methoxybenzyl; and
(11) acyl groups of the formula:

L—O—CO— in which L is an easily removable optionally substituted hydrocarbon group containing from 1 to 8 carbon atoms (e.g. 2,2,2-trichloroethyl, isobornyl, tertiary butyl, 1-methylcyclohexyl, 2-alkoxy tertiary butyl, benzyl, p-nitrobenzyl, or p-methoxybenzyl).

Alternatively, the substituent can be a diacyl group derived from a polybasic carboxylic acid containing from 4 to 12 carbon atoms, alkylidene containing from 1 to 6 carbon atoms, or arylmethylidene containing from 7 to 9 carbon atoms. In the above list of acyl groups, examples of Ar include furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, and dihydrophenyl, each being optionally substituted by halogen, alkyl containing from 1 to 3 carbon atoms, hydroxy, aminomethyl, or alkoxy containing from 1 to 3 carbon atoms.

Another amino substituents include a hydrocarbyl containing up to 20 carbon atoms (e.g. methyl, propyl, tertiary butyl, benzylidene, o-oxybenzylidene, trityl), silyl containing 1 to 10 carbon atoms (e.g. trialkylsilyl), sulfenyl (e.g. o-nitrophenylsulfenyl), which can, where possible, be unsaturated or substituted by an inert group e.g. halogen, alkyl, acyloxy, alkoxy or acylamino containing 1 to 8 carbon atoms, oxo, nitro and like substituents. The group convertible into amino or amido (e.g. azido, isocyanato, isocyano) is also included in the definition of the substituted amino. The silyl and sulfenyl groups are conventional protecting group for amino group. Two amino substituents on the amino can be combined to form a ring structure.

In the definition of the said 4-acylthio-3-amino-2-oxo-α-(substituted or unsubstituted)azetidine-1-acetic acid (I) is included a 3-substituted-4-thia-2,6-diaza-7-oxobicyclo[3,2,0]-hept-2-en-6-ylacetic acid which is a compound having combined 3-amino and 4-thio groups through an acyl.

The carboxy protecting group B can contain 1 to 20 carbon atoms, and can be an oxygen function such as, for example, alkoxy containing from 1 to 8 carbon atoms (e.g. methoxy, ethoxy, or tertiary butoxy), aralkoxy containing from 7 to 20 carbon atoms (e.g. benzyloxy, methoxybenzyloxy, nitrobenzyloxy, diphenylmethoxy, or trityloxy), mono- or bi-cyclic aryloxy (e.g. phenoxy or naphthyloxy), or organometaloxy (e.g. trimethylstannic oxy or trimethylsilyloxy), organic or inorganic acyloxy containing up to 8 carbon atoms or metal oxy of groups I, II, or III in the periodical table (e.g. sodiooxy, potassiooxy, or magnesiooxy); or B can be selected from sulfur functions such as those forming thiol ester, thiocarboxy, or like groups; nitrogen functions as these forming amides, hydrazides, azide or like groups; or B can be selected from other carboxy protecting groups.

These groups can, where possible, be interrupted by a hetero atom in their skeleton, or can be unsaturated or substituted by a substituent (e.g. the nitrogen, oxygen, sulfur, carbon, or phosphorus functions, or halogen).

Among carboxy protecting groups, are these forming haloalkyl esters containing from 1 to 5 carbon atoms, acylalkyl esters containing from 2 to 10 carbon atoms, alkoxyalkyl or aminoalkyl esters containing from 2 to 8 carbon atoms, the phenylester, aralkyl esters containing from 7 to 20 carbon atoms, ester with an oxime containing from 2 to 10 carbon atoms, N-alkoxyamide containing from 1 to 5 carbon atoms, imide with saccharin, imide with phthalimide, N,N'-diisobutylhydrazide, metal salts, alkylamine salts containing from 1 to 6 carbon atoms, or groups equivalent in effect to those groups (in the above, specified numbers of carbon atoms are for group B).

Antibacterially preferred carboxy-protecting groups B include these which from acyloxymethyl esters, phenacyl esters, the benzaldoxime ester, N,N-dimethylaminoethyl ester, methanesulfonylethyl ester, alkali metal salts, alkaline earth metal salts, acylated alkaline earth metal salts, and other groups equivalent in effect to these groups. Preferred carboxy protecting groups B include benzhydryloxy, p-nitrobenzyloxy, p-methoxybenzyloxy, 2,2,2-trichloroethoxy, and alkali metal oxy.

The process of this invention can be carried out by treating the 4-acylthio compound (I) with a salt of metal belonging to the group Ib or IIb of the periodical table to afford the 4-metalthio compound (II).

The said salt of a metal belonging to the group Ib or IIb of the periodical table can be a salt of a metal belonging to the group Ib (e.g. copper, silver) or IIb (e.g. zinc, cadmium, mercury), or their mixtures capable of cleaving the acylthio group giving the objective metal substituted thio group. The salt can be a salt of the metal with an organic acid as aliphatic acid (e.g. formic acid, acetic acid, propionic acid, succinic acid, oleic acid, lauric acid, stearic acid), aromatic carboxylic acid (e.g. benzoic acid, salicyclic acid, naphthenic acid), sulfonic acid (e.g. phenolsulfonic acid, toluene-p-sulfonic acid, trifluoromethanesulfonic acid, methanesulfonic acid), or other organic acids (e.g. citric acid, lactic acid, oxalic acid, trifluoroacetic acid); or inorganic acid as mineral acid (e.g. chloric acid, perchloric acid, bromic acid, iodic acid, periodic acid, sulfurous acid, persulfuric acid, selenic acid, nitric acid, nitrous acid, arsenic acid, phosphoric acid, pyrophosphoric acid, carbonic acid), or other inorganic acids (e.g. boric acid, sulfamic acid, carbamic acid), or double salts or complex salts (e.g. nitroprusside salts, silicofluoride, fluoroborate, a complex of mineral acid salts with alkali metal salts or ammonium salts), or their mixtures.

Among these salts, the salts highly soluble in the reaction medium, highly dissociating salts of strong acids, and the salts of silver or mercury having higher ability to capture the produced thio group, are more preferable. Specific examples of the preferable salts include $AgClO_4$, $AgIO_4$, $AgPF_6$, $CF_3COOAg$, $CF_3SO_3Ag$, $AgBF_4$, $CH_3SO_3Ag$, $AgNO_3$, $CH_3COOAg$, $Hg(ClO_4)_2$, $Hg(IO_4)_2$, $Hg(ClO_3)_2$, $Hg(PF_6)_2$, $(CF_3COO)_2Hg$, $(CF_3SO_3)_2Hg$, $Hg(BF_4)_2$, $(CH_3SO_3)_2Hg$, $Hg(NO_3)_2$, $(CH_3COO)_2Hg$, $Cu(ClO_4)_2$, $Zn(ClO_4)_2$, $Zn(BF_4)_2$, $Cd(NO_3)_2$, and $ZnSiF_6$.

The reaction is satisfactorily effected preferably in a solvent, at room temperature or cooled or elevated temperature. The said solvent can preferably be polar organic solvent (e.g. alcohol, ketone, ether, amide, sulfoxide, nitrile, ester) or water, or their mixtures, which can contain other organic solvent, catalyzer, or radical initiator, and if required under irradiation of light, for smooth reaction. The solvent system in which the produced metalthio compounds are less soluble is preferable for simpler isolation of the product. The solvent system in which the metalthio compounds are soluble (e.g. methylene chloride, chloroform) is preferable for the chromatographic separation, or successive treatment of the next step.

The solvent for the reaction medium can be a hydrocarbon (e.g. pentane, hexane, benzene, toluene), halohydrocarbon (e.g. methylene chloride, chloroform, carbon tetrachloride, dichlorobenzene), ester (e.g. ethyl acetate, butyl acetate, methyl benzoate, butyl acetate, methyl benzoate), ketone (e.g. acetone, cyclohexanone, benzophenone), ether (e.g. diethyl ether, ethyleneglycol dimethyl ether, tetrahydrofuran, tetrahydropyrane, dioxane, morpholine, anisole), alcohol (e.g. methanol, ethanol, ethyleneglycol, benzylalcohol), carboxylic acid (e.g. acetic acid, propionic acid), base (e.g. butylamine, triethylamine, pyridine, picoline), amide (e.g. dimethylformamide, dimethylacetamide, hexamethylphosphorotriamide), nitrile (e.g. acetonitrile, benzonitrile), nitrohydrocarbon, sulfoxide, (e.g. dimethylsulfoxide), water, liquid ammonia solvents, or their mixtures.

In a reaction medium in which the product is less soluble, the reaction product separates in the medium, which can be collected by filtration, washed, and dried to give the objective compound in high yield. In a reaction medium in which the reaction product is soluble, the reaction mixture can be evaporated to remove solvents and treated with a solvent in which the product is less soluble, or be isolated by conventional methods as extraction, washing, drying, and evaporating the solvent. For the purification is used recrystallization, reprecipitation, etc.

Thus prepared 4-metal thio compound (II) can be treated with a metal removing reagent to give the 4-mercapto compound (III).

The said metal removing reagent can be a thiol compound e.g. hydrogen sulfide, or a compound capable of forming insoluble compound with the said metal (e.g. hydrochloric acid, hydrobromic acid, or their salts), or compounds capable of removing metal by forming a complex. The reaction can be carried out in a solvent given above, at room temperature, cooled or elevated temperature. The product can be isolated by conventional methods from the reaction mixture by removing unreacted material, by-products, solvents, or other impurities, and be purified by conventional methods e.g. recrystallization, chromatography, reprecipitation.

The 4-metal thio compound (II) is a novel compound useful as an intermediate for synthesizing e.g. cephalosporin compounds by cyclization, and as a medicine.

More particularly, the present invention relates to a method for preparing a compound of the formula:

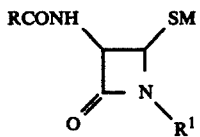

wherein R is methyl, phenyl, phenoxymethyl, or benzyl;

M is Ag or Hg$_\frac{1}{2}$;

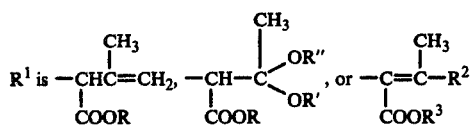

in which R' and R" each are alkyl or combined together form alkylene;

R$^2$ is hydroxy, methoxy, or methyl; and

R$^3$ is methyl, ethyl, t-butyl, trichloroethyl, benzyl, methoxybenzyl, nitrobenzyl, diphenylmethyl, or trimethylsilyl;

which comprises treating a compound of the formula:

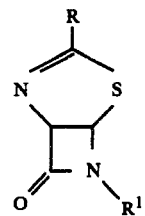

wherein R and R$^1$ are as defined above;

with a salt of metal selected from a group consisting of AgClO$_4$, AgIO$_4$, AgPF$_6$, CF$_3$COOAg, CF$_3$SO$_3$Ag, AgBF$_4$, CH$_3$SO$_3$Ag, AgNO$_3$, CH$_3$COOAg, Hg(ClO$_4$)$_2$, Hg(IO$_4$)$_2$, Hg(ClO$_3$)$_2$, Hg(PF$_6$)$_2$, (CF$_3$COO)$_2$Hg, (CF$_3$SO$_3$)$_2$Hg, Hg(BF$_4$)$_2$, (CH$_3$SO$_3$)$_2$Hg, Hg(NO$_3$)$_2$, and (CH$_3$COO)$_2$Hg.

Following examples illustrate some specific embodiments of this invention. They are not intended to limit the scope thereof.

EXAMPLE 1

To a solution of methyl 4-cyclopropylmethoxycarbonylthio-3-phthalimido-2-oxo-α-isopropylideneazetidine-1-acetate (734 mg) in methanol (3 ml) is added a solution of silver perchlorate (464 mg) in methanol (3 ml), and the mixture is stirred at room temperature under argon atmosphere. After 8 hours, the separated substance is collected by filtration, and washed with ether. The crystals are dissolved in methylene chloride, filtered through a layer of silica gel, evaporated, and recrystallized from a mixture of ether and pentane. The obtained crystals (546 mg) are silver salt at the mercapto of methyl 4-mercapto-3-phthalimido-2-oxo-α-isopropylideneazetidine-1-acetate. m.p. 196°–198° C. Yield: 73%.

EXAMPLE 2

To a solution of methyl 4-benzoylthio-3-phthalimido-2-oxo-α-isopropenylazetidine-1-acetate (464 mg) in dioxane (8 ml) is added a solution of silver perchlorate (456 mg) in methanol (2 ml), and the mixture is stirred at room temperature under nitrogen atmosphere. After 10 hours, the reaction mixture is concentrated after addition of methanol, and the separated silver salt at the mercapto of methyl 4-mercapto-3-phthalimido-2-oxo-α-isopropenylazetidine-1-acetate is collected by filtration. m.p. 165°–169° C. Crop: 401 mg. Yield: 86%.

EXAMPLE 3

To a solution of methyl 4-phenylacetylthio-3-phthalimido-2-oxo-α-(1-methoxyethylidene)azetidine-1-acetate (429 mg) in acetone (3 ml) is added a solution of silver perchlorate (334 mg) in methanol (2 ml), and the mixture is stirred at room temperature under nitrogen atmosphere. After 20 hours, the reaction mixture is diluted with methanol, and concentrated. The residue is dissolved in methylene chloride, diluted with a mixture of ether and pentane to separate crystals of silver salt at the mercapto of methyl 4-mercapto-3-phthalimido-2-oxo-α-(1-methoxyethylidene)azetidine-1-acetate (189 mg), which are collected by filtration. Yield 76%.

EXAMPLE 4

In the procedure of Example 3, the said silver perchlorate is substituted with silver nitrate (265 mg) or silver acetate (260 mg) to give silver salt at the mercapto of methyl 4-mercapto-3-phthalimido-2-oxo-α-(1-methoxyethylidene)-azetidine-1-acetate.

EXAMPLE 5

To a solution of 4-acetylthio-3-acylamino-2-oxo-α-substituted azetidine-1-acetate in a solvent is added powder or solution of the silver salt, and the mixture is stirred at room temperature under nitrogen or argon as an inert gas. After the reaction, when the objective compound separated, the product is collected by filtration, washed, and dried to give the product; and when the objective compound does not separate, if required after concentration, less dissolving solvent is added to separate the objective compound.

The product is a silver salt at the mercapto of 4-mercapto-3-acylamino-2-oxo-α-substituted azetidine-1-acetate.

The reaction conditions and the physical constants of the products are listed in Tables I and II. In the table, MeOH is for methanol, Di is for dioxane, EtOH is for ethanol, DMSO is for dimethylsulfoxide, and Ph is for phenyl.

EXAMPLE 6

To a solution of 3-substituted-4-thia-2,6-diaza-7-oxo-α-substituted bicyclo[3,2,0]hept-2-en-6-ylacetate in a solvent is added silver salt, and the mixture is stirred at room temperature under nitrogen or argon as inert gas. After the reaction, when the objective compound separated, the product is collected by filtration; and when the product did not separate, if required after concentration, less dissolving solvent is added to separate the objective compound.

The product is a silver salt at the mercapto of 4-mercapto-3-acylamino-2-oxo-α-substituted azetidine-1-acetate.

The reaction conditions are listed in Table III. Abbreviations and the physical constants are identical with these of Example 5, or Table II.

EXAMPLE 7

A silver salt at 4-mercapto of 4-mercapto-3-acylamino-2-oxo-α-substituted azetidine-1-acetate is dissolved in a solvent, and to the mixture is introduced hydrogen sulfide gas at room temperature until complete precipitation. Then the reaction mixture is bubbled with nitrogen gas to purge excessive hydrogen sulfide, and filtered to remove insoluble silver sulfide. Concentration of the filtrate gives a 4-mercapto-3-acylamino-2-oxo-α-substituted azetidine-1-acetate.

The reaction conditions and the physical constants of the products are given in Tables IV and V. The abbreviations are same with these in Example 5.

EXAMPLE 8

To a solution of a silver salt at 4-mercapto of 2,2,2-trichloroethyl 4-mercapto-3-phenoxyacetamido-2-oxo-α-(1,1-dimethoxyethyl)azetidine-1-acetate (57 mg) in chloroform (5 ml) is added 10% hydrochloric acid (0.5 ml), and the mixture is stirred at room temperature for 10 minutes. After removing insoluble material by filtration, the reaction mixture is concentrated to give 2,2,2-trichloroethyl 4-mercapto-3-phenoxyacetamido-2-oxo-α-(1,1-dimethoxyethyl)azetidine-1-acetate (40 mg). Yield: 94.2%.

EXAMPLE 9

According to the methods similar to these of Examples 5 to 8, the following compounds are prepared from the corresponding 4-acetylthioazetidineacetic acid derivatives or thiadiazabicycloheptaneacetic acid derivatives:

(1) p-methoxybenzyl 4-mercapto-3-(2,2,2-trichloroethoxycarbonyl)amino-2-oxo-α-(1-hydroxyethylidene)azetidine-1-acetate;

(2) 4-mercapto-3-benzyloxycarbonylamino-2-oxo-α-isopropylideneazetidine-1-acetic acid;

(3) p-bromophenacyl 4-mercapto-3-(o-nitrophenylsulfenyl)-amino-2-oxo-α-isopropenylazetidine-1-acetate;

(4) acetoxymethyl 4-mercapto-3-(N-tertiary butoxycarbonyl-α-phenylglycyl)amino-2-oxo-α-(1-methoxyethylidene)azetidine-1-acetate;

(5) p-nitrobenzyl 4-mercapto-3-[N-tertiary butoxycarbonyl-α-(1,4-cyclohexadien-1-yl)glycyl]amino-2-oxo-α-(1-hydroxyethylidene)azetidine-1-acetate;

(6) 2,2,2-trichloroethyl 4-mercapto-3-[N-2,2,2-trichloroethoxycarbonyl)-α-(p-hydroxyphenyl)glycyl]amino-2-oxo-α-(1-methoxymethylethylidene)azetidine-1-acetate;

(7) p-bromophenacyl 4-mercapto-3-(2,2-dimethyl-4-phenyl-5-oxoimidazolidin-1-yl)-2-oxo-α-(1-hydroxyethylidene)azetidine-1-acetate;

(8) sodium 4-mercapto-3-thienylacetamido-2-oxo-α-(1-chloroethylidene)azetidine-1-acetate;

(9) p-nitrobenzyl 4-mercapto-3-tetrazolylacetamido-2-oxo-α-(1-hydroxyethylidene)azetidine-1-acetate; and

(10) β-iodoethyl 4-mercapto-3-cyanoacetamido-2-oxo-α-(1-cyclopropylmethoxycarboxyethylidene)azetidine-1-acetate.

TABLE I

| Reaction No. | (I) R$_1$ | R$_2$ | R$_3$ | (I) (mg) | Silver salt (mg) | Solvent (ml) | Temp. | Reaction time (hr) | (II) Crop (mg) | Yield (%) |
|---|---|---|---|---|---|---|---|---|---|---|
| 1 | phthalimido | =C(CH$_2$)(CH$_3$) | —CH$_3$ | 719 | AgClO$_4$ 518 | MeOH 6 | rt | 6 | 636 | 76.2 |
| 2 | phthalimido | =C(CH$_3$)(CH$_3$) | —CH$_3$ | 402 | AgClO$_4$ 620 | MeOH+Di 7+8 | rt | 12 | 388 | 83.1 |

TABLE I-continued $$\underset{(I)}{\overset{R_1}{\underset{O}{\bigsqcup}}\overset{SCOCH_3}{\underset{N}{\bigsqcup}}\overset{}{\underset{COOR_3}{\bigsqcup}}R_2} \xrightarrow{Ag\text{-salt}} \underset{(II)}{\overset{R_1}{\underset{O}{\bigsqcup}}\overset{SAg}{\underset{N}{\bigsqcup}}\overset{}{\underset{COOR_3}{\bigsqcup}}R_2}$$

| Reaction No. | $R_1$ (I) | $R_2$ | $R_3$ | (mg) | Silver salt (mg) | Solvent (ml) | Temp. | Reaction time (hr) | (II) Crop (mg) | Yield (%) |
|---|---|---|---|---|---|---|---|---|---|---|
| 3 | phthalimido | =C(CH$_3$)OH | —CH$_3$ | 2000 | AgClO$_4$ 4000 | MeOH+Di 30+30 | rt | 5 | (1500 | 84)* |
| 4 | phthalimido | =C(CH$_3$)OH | —CH$_3$ | 100 | F$_3$CSO$_3$Ag 190 | MeOH+Di 2.4+0.7 | rt | 8 | 70 | 60 |
| 5 | phthalimido | =C(CH$_3$)OH | —CH$_3$ | 100 | F$_3$CCOOAg 160 | MeOH+Di 2.4+0.7 | rt | 8 | 41 | 35 |
| 6 | phthalimido | =C(CH$_3$)OCH$_3$ | —CH$_3$ | 1160 | AgClO$_4$ 1200 | MeOH 25 | rt | 7 | (710 | 68)* |
| 7 | phthalimido | =C(CH$_3$)Cl | —CH$_3$ | 1269 / 429 | AgClO$_4$ 1245 / AgClO$_4$ 400 | MeOH+Di 12+13 / MeOH+Di 6+4 | rt / rt | ON** / ON** | 902 / (351 | 62 / 90.8)* |
| 8 | PhOCH$_2$CONH— | =C(CH$_2$)CH$_3$ | —CHPh$_2$ | 127 | AgClO$_4$ 90 | MeOH 2 | rt | 2 | (52 | 41.7)* |
| 9 | PhOCH$_2$CONH— | =C(CH$_3$)OH | —CHPh$_2$ | 112 | AgClO$_4$ 160 | MeOH 3 | rt | 4 | (49 | 47.1)* |
| 10 | PhOCH$_2$CONH— | =C(CH$_3$)OCH$_3$ | —CHPh$_2$ | 314 | AgClO$_4$ 250 | MeOH 6 | rt | 5 | (112 | 38.3)* |
| 10' | PhOCH$_2$CONH— ($R_2$ isomer) | =C(OCH$_3$)CH$_3$ | —CHPh$_2$ | 238 | AgClO$_4$ 195 | MeOH 4 | rt | 5 | (87 | 39.3)* |
| 11 | PhOCH$_2$CONH— | =C(CH$_3$)OCH$_3$ | —CH$_2$CCl$_3$ | 78 | AgClO$_4$ 60 | MeOH 2 | rt | 7 | 54 | 64 |
| 12 | PhOCH$_2$CONH— | =C(CH$_2$)CH$_3$ | —CH$_2$CCl$_3$ | 320 | AgClO$_4$ 187 | MeOH 6 | rt | 2 | 180 | 51 |
| 13 | PhOCH$_2$CONH— | =C(CH$_3$)OH | —CH$_2$CCl$_3$ | 350 | AgClO$_4$ 152 | MeOH 7 | rt | 2 | 175 | 50 |
| 14 | PhOCH$_2$CONH— | =C(CH$_3$)OCH$_3$ | —CH$_2$C$_6$H$_4$NO$_2$ | 54.4 | AgClO$_4$ 34.9 | MeOH 1 | rt | 3 | 50 | 82.2 |
| 15 | PhOCH$_2$CONH— | =C(CH$_2$)CH$_3$ | —CH$_2$C$_6$H$_4$NO$_2$ | 58 | AgClO$_4$ 89 | MeOH 1 | rt | 5 | 46 | 71 |
| 16 | PhCH$_2$CONH— | =C(CH$_2$)CH$_3$ | —CH$_2$CCl$_3$ | 157 | AgClO$_4$ 145 | MeOH 1 | rt | 4 | 112 | 63 |
| 17 | PhOCH$_2$CONH— | =C(CH$_3$)OSO$_2$CH$_3$ | —CHPh$_2$ | 128 | AgClO$_4$ 83 | MeOH 2 | rt | 4 | (60 | 50)* |
| 18 | PhOCH$_2$CONH— | =C(CH$_3$)Cl | —CH$_2$CCl$_3$ | 325 | AgClO$_4$ 293 | MeOH 9 | rt | ON** | 250 | 68.7 |
| 19 | PhOCH$_2$CONH— | =C(CH$_3$)OCOCH$_2$-cyclopropyl | —CH$_2$CCl$_3$ | 195 | AgClO$_4$ 130 | MeOH 5 | rt | 15 | 140 | 65.0 |

*Yield of thiol derivative after substitution of Ag with H.
**ON is for keeping standing overnight.
rt: rt is for room temperature.

TABLE II (Silver salts) (II)

structure: R₁ and S-Ag on a β-lactam ring with N attached to C(R₂)(COOR₃)

| No. | R₁ | R₂ | R₃ | m.p.(° C) | IR: $\nu_{max}^{CHCl_3}$(cm$^{-1}$) | NMR: $\delta^{CDCl_3}$(60Mc) (Numbers in parentheses are coupling constants in Hz) |
|---|---|---|---|---|---|---|
| 1 | phthalimido | =C(CH₂)(CH₃) | —CH₃ | 165–169° C(d) [α]$_D^{23}$ −248° | — | — |
| 2 | phthalimido | =C(CH₃)(CH₃) | —CH₃ | 193–198° C(d) | — | — |
| 3 | phthalimido | =C(CH₃)(OH) | —CH₃ | — | — | — |
| 4 | phthalimido | =C(CH₃)(OCH₃) | —CH₃ | — | — | — |
| 5 | phthalimido | =C(CH₃)(Cl) | —CH₃ | 194–198° C(d) | 1787,1777,1727, 1617. | 2.53s3H,3.65s3H, 5.50d(5)1H, 5.63d(5)1H,7.85m4H [DMSO$_d^6$+CDCl₃(1:1)] |
| 6 | PhOCH₂C(O)NH— | =C(CH₂)(CH₃) | —CHPh₂ | powder | — | — |
| 7 | PhOCH₂C(O)NH— | =C(CH₃)(OH) | —CHPh₂ | — | — | — |
| 8 | PhOCH₂C(O)NH— | =C(CH₃)(OCH₃) | —CHPh₂ | — | — | — |
| 9 | PhOCH₂C(O)NH— | =C(CH₃)(OCH₃) | —CH₂CCl₃ | powder | 3420,1762,1722, 1685. | 2.33s3H,3.90s3H,4.54s2H, 4.57+4.83ABq(12)2H, 5.0–5.33m2H,6.87–7.43m5H, 7.77d(7)1H. |
| 10 | PhOCH₂C(O)NH— | =C(CH₂)(CH₃) | —CH₂CCl₃ | powder | 3425,1770,1690, 1680. | 2.03s3H,4.50s2H,4.84d(2)2H,5.03s1H,5.20brs2H, 5.36d(4)1H,5.75dd(7;4)1H,6.82–7.40m5H,7.71d(7)1H. |
| 11 | PhOCH₂C(O)NH— | =C(CH₃)(OH) | —CH₂CCl₃ | powder | 3422,1775,1693, 1677,1600. | 2.27s3H,4.55s2H, 4.62+4.95ABq(11)2H, 5.08–5.30m1H, 5.60–5.80m1H, 6.70–7.62m6H, 11.85s1H. |
| 12 | PhOCH₂C(O)NH— | =C(CH₃)(OCH₃) | —CH₂C₆H₄NO₂ | 124–125° C(d) | 3410,1774,1710, 1664,1603. | — |
| 13 | PhOCH₂C(O)NH— | =C(CH₂)(CH₃) | —CH₂C₆H₄NO₂ | 103–108° C | 3420,1768,1737, 1686,1601,1590, 1524,1497. | 1.85s3H,4.65s2H, 5.32s2H,4.9–5.7m5H, 6.7–8.4m9H,8.98d(8)1H . (DMSO$_d^6$) 6) . A-60 |
| 14 | PhOCH₂C(O)NH— | =C(CH₃)(OH) | —CH₂C₆H₄NO₂ | — | — | — |
| 15 | PhOCH₂C(O)NH— | —C(CH₃)(OCH₃)(OCH₃) | —CH₂CCl₃ | powder | 3420,1788,1680, 1600. | 1.57s3H,3.22s3H, 3.27s3H,4.48s3H, 4.81s2H,5.24–5.50m2H, 6.76–7.26m5H, 7.83d(8)1H. |
| 16 | PhCH₂C(O)NH— | =C(CH₂)(CH₃) | —CH₂CCl₃ | foam | 3420,1765,1750, 1675,1650. | — |
| 17 | PhOCH₂C(O)NH— | =C(CH₃)(Cl) | —CH₂CCl₃ | powder | 3425,1778,1710, 1664. | 2.50s+2.53s3H, 4.47s2H,4.62+4.89ABq(12)2H,5.08–5.40m1H, 5.58–5.81m1H, 6.90–7.40m5H, 7.83d1H. |

TABLE II-continued

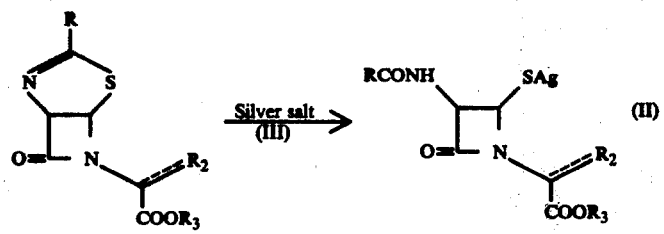

(Silver salts) (II)

| No. | R₁ | R₂ | R₃ | m.p.(° C) | IR:ν$_{max}^{CHCl_3}$(cm⁻¹) | NMR: δ$^{CDCl_3}$(60Mc) (Numbers in parentheses are coupling constants in Hz) |
|---|---|---|---|---|---|---|
| 18 | PhOCH₂C(O)NH— | CH₃, O₂COCH₂-cyclopropyl | —CH₂CCl₃ | powder | 3420,1775,1750, 1720,1667. | — |

TABLE III $$\text{(III)} \xrightarrow{\text{Silver salt}} \text{(II)}$$

| Reaction No. | (III) | | | | Ag-salt (mg) | Solvent (ml) | Temp. | Reaction Time(hr) | Crop (mg) | (II) Yield (%) |
| | R | R₂ | R₃ | (mg) | | | | | | |
|---|---|---|---|---|---|---|---|---|---|---|
| 1 | PhOCH₂— | =C(CH₂)CH₃ | —CH₂CCl₃ | 4640 | AgClO₄ 2280 | Di+H₂O 50+10 | rt | 5 | 2950 | 50 |
| 2 | PhOCH₂— | =C(CH₂)CH₃ | —CHPh₂ | 1000 | AgClO₄ 830 | Di+H₂O 10+25 | rt | 7 | (755 | 60.3)* |
| 3 | PhOCH₂— | =C(CH₃)OCH₃ | —CH₂CCl₃ | 96 | AgClO₄ 50 | Di+H₂O 2+0.5 | rt | 20 | 80 | 66.2 |
| 4 | PhOCH₂— | =C(CH₂)CH₃ | —CH₂C₆H₄NO₂ | 2577 | AgClO₄ 1190 | THF+H₂O+Di 25+5+10 | rt | 4 | 2198 | 97.8 |
| 5 | PhOCH₂— | =C(CH₂)CH₃ | —CH₂C₆H₄NO₂ | 467 | AgBF₄ 206 | THF+H₂O 6+1 | rt | 24 | 565 | 95.4 |
| 6 | PhCH₂— | =C(CH₂)CH₃ | —CH₂CCl₃ | 224 | AgClO₄ 105 | Di+H₂O 3+0.75 | rt | 7 | 258 | 90 |
| 7 | PhOCH₂— | =C(CH₃)OH | —CH₂C₆H₄NO₂ | 233 | AgClO₄ 124 | Di+H₂O 2+0.5 | rt | 6 | 218 | 73[1] |
| 8 | PhOCH₂— | =C(CH₃)OH | —CH₂C₆H₄NO₂ | 323 | AgBF₄ 294 | THF+Di+H₂O 4+1+1.2 | rt | 6 | 210 | 53 |
| 9 | PhOCH₂— | C(CH₃)(OCH₃)₂ | —CH₂CCl₃ | 1500 | AgClO₄ 670 | Di+H₂O 40+10 | 30° C | 5 | 1824 | 98 |
| 10 | PhOCH₂— | =C(CH₃)OH | —CH₂CCl₃ | 441 | AgClO₄ 217 | Di+H₂O 9.5+2.3 | rt | 6 | 375 | 78[2] |
| 11 | PhOCH₂— | =C(CH₃)OCH₃ | —CH₂CCl₃ | 384 | AgClO₄ 190 | Di+H₂O 8+2 | rt | 8 | 484 | 71 |

[1] The reaction medium is irradiated with W-lamp at the begining 5 minutes of the reaction.
[2] The reaction is carried out in the presence of catalytic amount of azobisisobutyronitrile

TABLE IV $$\text{(II)} \xrightarrow{H_2S} \text{(IV)}$$

where (II) is the silver thiolate azetidinone with $R_1$, S—Ag, $R_2$, COOR$_3$ substituents and (IV) is the corresponding thiol (SH).

| Reaction No. | (II) R$_1$ | R$_2$ | R$_3$ | (mg)[1] | (IV) Solvent (ml) | Temp. (°C.) | Crop (mg.) | Yield (%) |
|---|---|---|---|---|---|---|---|---|
| 1 | phthalimido-N— | CH$_2$=C(CH$_3$)– | —CH$_3$ | 300 | CHCl$_3$ 6 | 0 | 245 | 100 |
| 2 | phthalimido-N— | CH$_3$–C=CH(CH$_3$) | —CH$_3$ | 224 | CHCl$_3$ 6.6 | 0 | 145 | 84 |
| 3 | phthalimido-N— | CH$_3$–C=CH(OH) | —CH$_3$ | (Ex5-3) | CH$_2$Cl$_2$ — | rt | 1500 | (84)*** |
| 4 | phthalimido-N— | CH$_3$–C=CH(OCH$_3$) | —CH$_3$ | (Ex5-6) | CH$_2$Cl$_2$ 20 | rt | 710 | (68)*** |
| 5 | phthalimido-N— | CH$_3$–C=CH(Cl) | —CH$_3$ | (Ex5-7) | CHCl$_3$ — | rt | 351 | (90.8)*** |
| 6 | PhOCH$_2$C(=O)NH— | CH$_2$=C(CH$_3$)– | —CHPh$_2$ | (Ex5-8) / (Ex6-2) | CHCl$_3$ 20 / CHCl$_3$ — | rt / rt | 52 / 755 | (41.7)*** / (60.3)*** |
| 7 | PhOCH$_2$C(=O)NH— | CH$_3$–C=CH(OH) | —CHPh$_2$ | (Ex5-9) | CHCl$_3$ — | rt | 49 | (47.1)*** |
| 8 | PhOCH$_2$C(=O)NH— | CH$_3$–C=CH(OCH$_3$) | —CHPh$_2$ | (Ex5-10) | CHCl$_3$ — | rt | 112 | (38.3)*** |
| 9 | PhOCH$_2$C(=O)NH— | CH$_3$–CH(OCH$_3$)– | —CH$_2$CCl$_3$ | (Ex6-3) | CH$_2$Cl$_2$ | rt | — | — |
| 10 | PhCH$_2$C(=O)NH— | CH$_2$=C(CH$_3$)– | —CH$_2$CCl$_3$ | 330 | CHCl$_3$ 20 | rt | 230 | 90.6 |
| 11 | PhOCH$_2$C(=O)NH— | CH$_2$=C(CH$_3$)– | —CH$_2$C$_6$H$_4$NO$_2$ | 105 | CH$_2$Cl$_2$ 6 | −50 | 86 | 100 |
| 12 | PhOCH$_2$C(=O)NH— | CH$_3$–C(OCH$_3$)$_2$ | —CH$_2$CCl$_3$ | 57 | CHCl$_3$ 5 | rt | 40 | 94.2 |
| 13 | PhOCH$_2$C(=O)NH— | CH$_3$–C=CH(OH) | —CH$_2$CCl$_3$ | 69 | CH$_2$Cl$_2$ 5 | rt | 52 | 92 |
| 14 | PhOCH$_2$C(=O)NH— | CH$_3$–C=CH(OCH$_3$) | —CHPh$_2$ | 80 | CHCl$_3$ 5 | rt | 53 | 80 |
| 15 | PhOCH$_2$C(=O)NH— | CH$_3$–C=CH(OSO$_2$CH$_3$) | —CHPh$_2$ | (Ex5-17) | CH$_2$Cl$_2$ 2 | rt | 60 | (50)*** |

***Overall yield from preceding reaction.

[1] The example No. in the parentheses shows example number of the preceding reaction.

TABLE V (Thiols)

$$\text{(IV)} \quad \begin{array}{c} R_1 \quad SH \\ \diagup \quad \diagup \\ \text{structure with } \beta\text{-lactam, N-C(=R_2)COOR_3} \end{array}$$

Physical constants

| No. | $R_1$ | $R_2$ | $R_3$ | m.p.(°C) | IR: $\nu_{max}^{CHCl_3}$(cm$^{-1}$) | NMR: $\delta^{CDCl_3}$(60Mc) (Numbers in parentheses are coupling constants in Hz) |
|---|---|---|---|---|---|---|
| 1 | Phthalimido-N— | =C(CH$_3$)CH$_2$ | —CH$_3$ | oil | 1795,1750,1733 (CCl$_4$). | 1.95t(1)3H,1.96d(9.5)1H,3.37s3H, 4.96t(1)2H,5.04s1H, 5.22dd(90.5;5)1H,5.58d(5)1H, 6.48–7.46m4H C$_6$D$_6$. |
| 2 | Phthalimido-N— | =C(CH$_3$)CH$_3$ | —CH$_3$ | 155–158° [α]$_D^{24}$ –83.5° | 1792,1773,1722 (Nujol). | 2.11d(10.4)1H,2.29s3H,2.34s3H, 3.80c3H,5.47dd(10.4;5) 1H,5.69d(5)1H,7.85m4H. |
| 3 | Phthalimido-N— | =C(CH$_3$)OH | —CH$_3$ | 167.5–169° | 1785,1775,1725, 1668,1626. | 2.10d(10)1H,2.40s3H,3.86s3H, 5.37dd(10;5)1H,5.72d(5) 1H,7.70–8.05m4H,12.3s1H. |
| 4 | Phthalimido-N— | =C(CH$_3$)OCH$_3$ | —CH$_3$ | 169–171° | 1790,1776,1730, 1618. | 2.22d(10)1H,2.58s3H,3.78s3H, 3.94s3H,5.25dd(10;4)1H, 5.64d(4)1H. |
| 5 | Phthalimido-N— | =C(CH$_3$)Cl | —CH$_3$ | 146–149° | 1791,1781,1729, 1617. | 2.20d(10)1H,2.67s3H,3.88s3H, 5.59dd(10;4)1H,5.80d(4) 1H,7.9m4H. |
| 6 | PhOCH$_2$C(O)NH— | =C(CH$_3$)CH$_2$ | —CHPh$_2$ | oil | 3420,1770,1738, 1685. | 1.89s3H,1.92d(10)1H,4.56s2H, 4.93s2H,5.08m1H,5.20–5.65 m2H,6.80–7.55m16H. |
| 7 | PhOCH$_2$C(O)NH— | =C(CH$_3$)OH | —CHPh$_2$ | foam | 3420,1770,1700, 1683,1650. | 1.92d(10)1H,2.22s3H,4.66s2H, 5.16–5.50m2H,6.92–7.55m 16H,12.4s1H. |
| 8 | PhOCH$_2$C(O)NH— | =C(CH$_3$)OCH$_3$ | —CHPh$_2$ | oil | 3460,1780,1772, 1695. | 1.60d(10)1H,2.53s3H,3.80s3H, 4.60s2H,5.0–5.33m2H,6.85– 7.50m16H. |
| 9 | PhOCH$_2$C(O)NH— | =C(CH$_3$)OCH$_3$ | —CH$_2$CCl$_3$ | oil | 3430,1770,1730, 1690. | 2.16d(10)1H,2.36s3H,3.95s3H,4.58s2H, 4.68dd(20;12)2H, 5.04–5.52m2H,6.78–7.35m6H. |
| 10 | PhCH$_2$C(O)NH— | =C(CH$_3$)CH$_2$ | —CH$_2$CCl$_3$ | oil | 3420,1775,1758, 1674. | 1.92s3H,1.99d(10)1H,3.63s2H, 4.80s1H,4.73+4.90ABq(12.5) 2H,5.02–5.25m5H, 6.85t(8)1H,7.34s5H. |
| 11 | PhOCH$_2$C(O)NH— | =C(CH$_3$)CH$_2$ | —CH$_2$C$_6$H$_4$NO$_2$ | 50–51° | 3245,1765,1740, 1668,1597,906. | 1.91s3H,2.03d(8)1H,4.51s2H,4.80s1H, 4.99–5.10m2H,5.21s2H,5.26– 5.54m2H,5.62–6.11m9H. |
| 12 | PhOCH$_2$C(O)NH— | =C(CH$_3$)(OCH$_3$)$_2$ | —CH$_2$CCl$_3$ | oil | 3430,1785,1695. | 1.60s3H,2.00d(8)1H,3.27ss3H,H,3.30s3H, 4.50s1H,4.58s2H,4.78s2H,5.20– 5.65m2H,6.87–7.50m5H. |
| 13 | PhOCH$_2$C(O)NH— | =C(CH$_3$)OH | —CH$_2$CCl$_3$ | oil | 3422,1772,1692, 1678,1598. | 2.13d(9)1H,2.30s3H,4.60s2H,4.65+ 4.95ABq(11.5)2H,5.01– 5.50,m2H,6.89–7.50m6H,11.70s1H. |
| 14 | PhOCH$_2$C(O)NH— | =C(CH$_3$)OCH$_3$ | —CHPh$_2$ | foam | 3440,1773,1693, 1602. | 2.05d(9)1H,2.15s3H,3.92s2H, 4.59s2H,5.00–5.39m2H, 6.90–7.43m16H. |
| 15 | PhOCH$_2$C(O)NH— | =C(CH$_3$)OSO$_2$CH$_3$ | —CHPh$_2$ | foam | 3415,1775,1723, 1689,1358. | — |

What we claim is:

1. A process for preparing compounds having the formula:

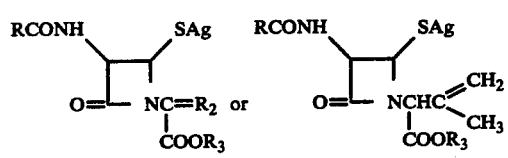

wherein R is phenoxymethyl or benzyl;

R₂ is 1-methoxyethylidene, 1-hydroxyethylidene, or 1,1-dimethoxyethylidene; and

R₃ is trichloroethyl, diphenylmethyl, p-nitrobenzyl, trityl, phenyl, naphthyl, or trimethylstannyl;

which comprises treating a compound of the following formula:

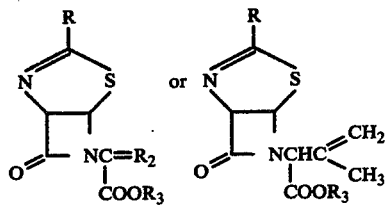

wherein R, R₂ and R₃ are as defined above,
with AgClO₄, AgBF₄, AgIO₄, AgPF₆, CF₃COOAg, CH₃SO₃Ag, CF₃SO₃Ag, CH₃COOAg, or AgNO₃ in aqueous dioxane, aqueous tetrahydrofuran or mixtures thereof.

2. The process as claimed in claim 1 wherein the reaction is carried out in an additional solvent which is methanol, ethanol, propanol, butanol, methylene chloride, chloroform, or a mixture thereof.

3. The process according to claim 1 wherein the treatment is performed in the presence of azobisisobutyronitrile.

4. The process according to claim 1 wherein the treatment is performed under irradiation with a tungsten lamp.

5. The process of claim 1 wherein the treatment is performed at from room temperature to 30° C. for from 4 to 24 hours.